US007807844B2

(12) United States Patent
Fukuda et al.

(10) Patent No.: US 7,807,844 B2
(45) Date of Patent: Oct. 5, 2010

(54) TGF-β GENE EXPRESSION INHIBITOR

(75) Inventors: Noboru Fukuda, Tokyo (JP); Hirofumi Kishioka, Tokyo (JP); Hiroshi Sugiyama, Kyoto (JP)

(73) Assignees: Nihon University, Tokyo (JP); Gentier Biosystems, Inc., Tokyo (JP)

( * ) Notice: Subject to any disclaimer, the term of this patent is extended or adjusted under 35 U.S.C. 154(b) by 1253 days.

(21) Appl. No.: 10/570,159

(22) PCT Filed: Sep. 3, 2004

(86) PCT No.: PCT/JP2004/012854

§ 371 (c)(1),
(2), (4) Date: Mar. 1, 2006

(87) PCT Pub. No.: WO2005/023248

PCT Pub. Date: Mar. 17, 2005

(65) Prior Publication Data

US 2008/0103187 A1    May 1, 2008

(30) Foreign Application Priority Data

Sep. 4, 2003  (JP)  ............................ 2003-312365

(51) Int. Cl.
C00D 403/02   (2006.01)
C07D 233/00   (2006.01)
C07D 487/04   (2006.01)
C07D 233/34   (2006.01)

(52) U.S. Cl. ..................... 548/314.7; 514/183; 514/359

(58) Field of Classification Search ........................ None
See application file for complete search history.

(56) References Cited

U.S. PATENT DOCUMENTS

2004/0171799 A1   9/2004   Sugiyama et al.
2004/0209254 A1   10/2004  Henderson

FOREIGN PATENT DOCUMENTS

| JP | 3045706 B1 | 3/2000 |
| JP | 2001-136974 A | 5/2001 |
| WO | WO-02/08468 A1 | 1/2002 |
| WO | WO-03/000683 A1 | 1/2003 |

OTHER PUBLICATIONS

White et al., Chemistry & Biology , vol. 4, No. 8, 569-578, (1997) -From Applicant's IDS.*
White et al., Chemistry & Biology, vol. 4, No. 8,569-578, (1997), from Applicant's submitted ID.*
Fukuda, N., Gene therapy for arterial proliferative disease and progressive renal diseases by nucleic acid medicines, Nichidai Igaku Zasshi, Jul. 2003, vol. 62, No. 7, pp. 329 to 336, particularly, p. 335, left column.
Piek et al., FASEB J., vol. 13, No. 15, pp. 2105-2124, 1999.

Bataller R. et al., Gastroenterology, vol. 118, No. 6, 2000, pp. 1149-1156.
Watanabe et al., Gendai Iryo, vol. 35, No. 2, 2003, pp. 86-91, with English translation.
YamamotoT. et al., Kidney International, vol. 49, No. 2, 1996, pp. 461-469.
Border WA et al., Kidney International, vol. 51, No. 5, 1997, pp. 1388-1396.
Ono et al., Circulation, 1998, vol. 98, pp. 149-156.
Giri SN et al., Thorax, 1993, vol. 48, No. 10, pp. 959-966.
Makino N. et al., Gendaiiryo, vol. 35, No. 2, 2003, pp. 111-116, with English translation.
Mori et al., Journal of Cellular Physiology, vol. 181, pp. 153-159, 1999.
Reilly J. et al., Clinical Haematology, vol. 11, No. 4, 1998, pp. 751-767.
Martyre M C et al., British Journal of Haematology, 1991, vol. 77, pp. 80-86, 1991.
Rameshwar P. et al., American Journal of Hematology, vol. 59, No. 2, 1998, pp. 133-142.
Rameshwar P. et al., The Journal of Immunology, vol. 165, No. 4, pp. 2271-2277, 2000.
Shigeki et al., FASEB Journal, vol. 16, pp. 1967-1969, 2002.
Trauger et al., Nature, vol. 382, No. 6591, pp. 559-561, 1996.
White et al., Chemistry & Biology, vol. 4, No. 8, pp. 569-578, 1997.
Dervan, Bioorganic & Medicine Chemistry, vol. 9, pp. 2215-2235, 2001.
White et al., Nature, vol. 391, pp. 468-471, 1998.
Gottesfeld et al., Nature, vol. 387, pp. 202-205, 1997.
Dickinson et al., Proc. Natl. Acad. Sci. USA, vol. 95, pp. 12890-12895, 1998.
Lee et al., Proc. Natl. Acad. Sci. USA, vol. 93, pp. 2570-2575, 1996.
Dickinson et al., Biochemistry, vol. 38, pp. 10801-10807, 1999.
Mapp et al., Proc. Natl. Acad. Sci. USA, vol. 97, pp. 3930-3935, 2000.
Fukuda, Gene Therapy for Arterial Proliferative Diseases and Progressive Renal Diseases by Nucleic Acid Medicines, vol. 62, No. 7, pp. 329-336, 2003.
Janssen et al., Molecular Cell, vol. 6, pp. 1013-1024, 2000.
Janssen et al., Molecular Cell. vol. 6, pp. 999-1011, 2000.
Hu et al., Journal of Hypertension, vol. 19, No. 2, pp. 203-212, 2001.
Teng et al., Cardiovascular Research, vol. 48, pp. 138-147, 2000.

(Continued)

*Primary Examiner*—Cecilia Tsang
*Assistant Examiner*—Thomas S Heard
(74) *Attorney, Agent, or Firm*—Birch, Stewart, Kolasch & Birch, LLP

(57) ABSTRACT

A TGF-β gene expression inhibitor containing a pyrrole-imidazole polyamide having N-methylimidazole unit (hereinafter also referred to as Py), N-methylimidazole unit (hereinafter also referred to as Im) and γ-aminobutyrate unit which can be holded into an U-shaped conformation at the γ-aminobutyrate unit in the minor groove in a double helix region (hereinafter referred to as the target region) containing a complementary chain corresponding to the sequence at the −557 to −536 in the base sequence of a human transforming growth factor β1 (hereinafter also referred to as hTGF-β1) promoter, either as a whole or a part thereof: TAAAG-GAGAGCAATTCT-TACAG (SEQ ID NO: 1) wherein a Py/Im pair corresponds to a C-G base pair, an Im/Py pair corresponds to a G-C base pair, and Py/Py pairs correspond respectively to an A-A base pair and a T-A base pair.

5 Claims, 4 Drawing Sheets

OTHER PUBLICATIONS

Lee et al., Cell, vol. 67, pp. 1241-1250, 1991.
Starr et al., Cell, vol. 67, pp. 1231-1240, 1991.
Courey et al., Cell, vol. 55, pp. 887-898, 1988.
Javahery et al., Molecular and Cellular Biology, vol. 14, No. 1, pp. 116-127, 1994.
Lo et al., Gene, vol. 182, pp. 13-22, 1996.
Romeo et al., Gene, vol. 189, pp. 289-295, 1997.
Kim et al., The Journal of Biological Chemistry, vol. 264, No. 1, pp. 402-408, 1989.
Kadonaga et al., Cell, vol. 51, pp. 1079-1090, 1987.
Kim et al., The Journal of Biological Chemistry, vol. 264, No. 12, pp. 7041-7045, 1989.
Kim et al., The Journal of Biological Chemistry, vol. 264, No. 32, pp. 19373-19378, 1989.
Kim et al., Molecular and Cellular Biology, pp. 1492-1497, vol. 10, No. 4, 1990.
Birchenall-Roberts et al., Molecular and Cellular Biology, vol. 10, No. 9, pp. 4978-4983, 1990.
Aso et al., The EMBO Journal, vol. 13, No. 2, pp. 435-445, 1994.
Mack et al., Nature, vol. 363, pp. 281-283, 1993.
Merino et al., Nature, vol. 365, pp. 227-232, 1993.
Berger et al., Molecular Cell, vol. 8, pp. 263-268, 2001.
McKeown, Annu. Rev. Cell Biol., vol. 8, pp. 133-155, 1992.
Decker et al., Trends Biochem Sci., vol. 19, pp. 336-340, 1994.
Kozak, Annu. Rev. Cell Biol., vol. 8, pp. 197-225, 1992.
Gottesfeld et al., Journal of Molecular Biology, vol. 321, pp. 249-263, 2002.
Gottesfeld et al., Journal of Molecular Biology, vol. 309, pp. 615-629, 2001.

* cited by examiner

POLYAMIDE-OLYGONUCLEOTIDE COMPOUND →
DOUBLE STARANDED OLYGONUCLEOTIDE →
SINGLE STARANDED OLYGONUCLEOTIDE →

FIG. 4
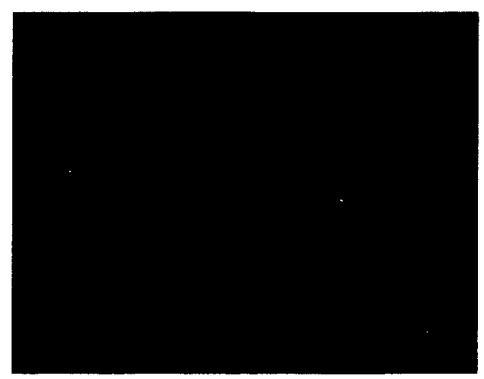
FIG. 5
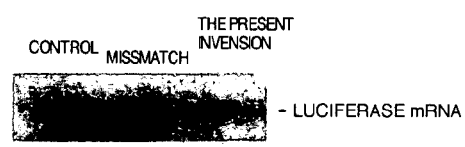
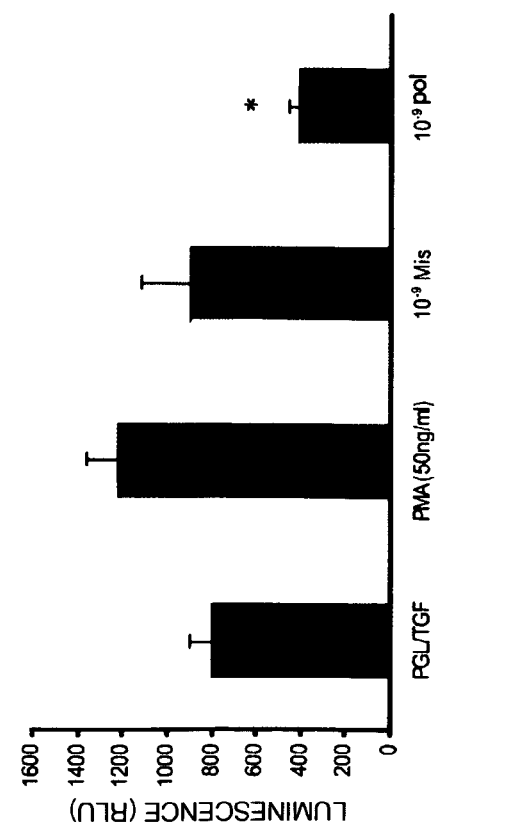
FIG. 6

TGF-β GENE EXPRESSION INHIBITOR

TECHNICAL FIELD

The present invention relates to a transforming growth factor TGF-β gene expression inhibitor, a therapeutic drug for diseases related to TGF-β and a new pyrrole-imidazole polyamide. More specifically, the present invention relates to the TGF-β gene expression inhibitor containing a pyrrole-imidazole polyamide having a specific structure.

BACKGROUND ART

Essential hypertension induces serious complications such as cerebral stroke, ischemic heart disease, nephrosclerosis and the like, and these complications are basically related to angiopathy due to excessive growth of vascular smooth muscle cells (VSMC) and are targets of hypertension therapy. Further, after percutaneous transluminal coronary angioplasty (PTCA) for treatment of angina pectoris and myocardial infarction, restenosis occurs in about 40% of the cases, but there is no effective drug treatment therefor and is a big problem in the cardiovascular field. Histopathologically, it is known that TGF-β is involved in arterial proliferative diseases such as hypertensive vascular disease, neointimal formation after angioplasty and atherosclerosis. The cell growth in such diseases are thought to be suppressed by various mechanisms. One of the various mechanism is the inhibition of the transforming growth factor (TGF) expression.

TGF was discovered at first as a factor of mouse 3T3 cells transformed by Molony sarcoma virus (MSV) that converts normal cells to malignant cells, and is classified mainly to TGF-α and TGF-β. TGF-β is a part of the 112 amino acids at the C-terminal of the protein whose molecular weight is about 40,000 and which consists of 390-412 amino acids as a precursor and further forms a dimer (25 kDa) through a disulfide bond to have an activity.

TGF-β, which constitutes a protein family that controls growth and development of cells (non-patent document 1), is produced in various tissues such as blood vessels, platelets, liver, kidneys, heart muscle, lung, pancreas, skin, placenta, bone marrow and has a control activity on cell proliferation, extra-cellular matrix formation and immunity.

TGF-β suppresses proliferation of most of cells but has a 2 biphasic proliferating activity on mesenchymal cells such as fibroblast cells, vascular smooth muscle cells (VSMC) and the like. That is, in normal condition TGF-β suppresses the proliferation of these cells but stimulates the proliferation under the circumstances such as inflammation, mechanical stress and the like. These facts reveal that TGF-β is involved in neointimal formation after angiopathy by promoting the growth of VSMC and extra-cellular matrix formation. TGF-β is also involved in the formation of lesions of arteriosclerosis. Based on such information, it is believed that the local treatment of the blood vessel diseases aiming to control the effect of TGF-β could be effective to ease the arterial proliferative diseases described above.

Further, TGF-β is believed to be involved in the restenosis of renal artery after percutaneous renal angioplasty. These facts reveal that the specific TGF-β gene expression inhibitor of the present invention may be effective as a therapeutic drug for various proliferative vascular and stenotic diseases described above.

Further, astrocytes in the liver play an important role in the production of extracellular matrix in the process of fibril formation in the liver (non-patent document 2). The astrocytes are activated by TGF-β1, and the activated astrocytes induces TGF-β1 secretion from inflammatory cells in a damaged liver. At the same time the expression of the TGF-β1 receptor is enhanced in the activated astrocytes, and extracellular matrix proteins are increased by autocrine mechanism by TGF-β1 (non-patent document 3). These facts reveal that it is reasonable to assume the specific inhibitor of TGF-β1 gene expression of the present invention is effective as a therapeutic drug for various liver diseases described above.

Further, the expression of TGF-β is increased in parallel with the extracellular substrate in renal biopsy of model animals for nephropathies such as IgA nephropathy, focal glomerulosclerosis, crescentic nephritis, focal sclerotic lupus nephritis, diffuse proliferative lupus nephritis, diabetic nephropathy, hypertensive nephrosclerosis and the like and in renal biopsy tissue of patients of glomerulonephritis and diabetic nephropathy (non-patent document 4 and non-patent document 5). At the same time, Border et al. reported that administration of anti-TGF-β to Thy-1 nephritis rats inhibits accumulation of extracellular substrate in the renal glomeruli (non-patent document 5). These facts suggest that it is reasonable to assume the specific inhibitor of TGF-β1 gene expression of the present invention is effective as a therapeutic drug for various nephropathies described above.

Further, in the infarction focus at the scar forming stage in animal model of myocardial infarction, the expression of TGF-β is continuously elevated and involved in myocardial fibrillation (non-patent document 6). These facts suggest that it is reasonable to assume the specific inhibitor of TGF-β1 gene expression of the present invention is effective as a therapeutic drug for myocardial fibrillation after myocardial infarction.

Further, administration of anti-TGF-β antibodies and the soluble receptor of TGF-β to pulmonary fibrosis model animals improves pulmonary fibrosis (non-patent document 7). These facts suggest that it is reasonable to assume the specific inhibitor of TGF-β1 gene expression of the present invention is effective as a therapeutic drug for pulmonary fibrosis.

Further, there have been many reports on the high expression of TGF-β1 in human chronic pancreatitis, and administration of recombinant TGF-β to model animal of recurring acute pancreatitis induces fibril formation or high expression of the mRNA of fibronectin at the inflammation lesion of the pancreas. Conversely, it has been demonstrated that administration of a neutralizing antibody against TGF-β1, when pancreatitis model is prepared, inhibits the production of extracellular matrix and the expression of mRNA of I and III type collagen and fibronectine (non-patent document 8). These facts suggest that it is reasonable to assume the specific inhibitor of TGF-β1 gene expression of the present invention is effective as a therapeutic drug for fibril formation in chronic pancreatitis.

Further, it has been proposed that scleroderma may be caused by TGF-β, and Mori et al. reported that TGF-β induced fibrillation of the skin in model mice for dermal fibrillation (non-patent document 9). These facts suggest that it is reasonable to assume the specific inhibitor of TGF-β1 gene expression of the present invention is effective as a therapeutic drug for various skin fibrillation diseases.

Further, it has been reported that the expression of TGF-β mRNA is enhanced in megakaryocyte of bone marrow fibrosis patients (non-patent document 10), and the concentration of TGF-β in platelets takes a high value (non-patent document 11) and TGF-β concentration in plasma of the patients is significantly higher (non-patent document 12). According to Rameshwar et al., monocytes of bone marrow fibrosis patients activate, through adhesion, NF-k which induces IL-1 production, and IL-1 causes the bone marrow fibrosis by facilitating TGF-β production (non-patent document 13).

These facts suggest that it is reasonable to assume the specific inhibitor of TGF-β1 gene expression of the present invention is effective as a therapeutic drug for bone marrow fibrosis.

Further, it has been reported that in the cell culture system of androgenetic alopecia patients with frontal hair loss, male hormone induces TGF-β1 from dermal papilla cells, and this TGF-β1 inhibits the growth of epidermal cells (non-patent document 14). These facts suggest that it is reasonable to assume the specific inhibitor of TGF-β1 gene expression of the present invention is effective as a therapeutic drug for androgenetic alopecia with frontal hair loss.

The method of inactivating a gene function in the reverse genetics has been used to analyze a specific gene function but also has a potential to be utilized in therapeutic application for virus infection, cancer and other diseases caused by abnormal gene expression. That is, it is known that the inactivation of the gene function can be achieved at DNA level by homologous recombination or at RNA level by antisense oligodeoxyribonucleotides and ribozymes. However, the methods using antisense oligonucleotides and ribozymes have problems that the target sequence is limited, the transfer of the antisense oligonucleotides and ribozymes to tissues and cells is inefficient, and they are prone to degradation by ribonuclease.

On the other hand, it has been reported that pyrrole-imidazole polyamides (hereinafter also referred to as Py-Im polyamide), unlike (deoxy)ribonucleotide reagents such as antisense reagents and ribozymes, can specifically recognize a DNA sequence and control the expression of a specific gene extracellularly.

Pyrrole-imidazole polyamides are a group of synthetic small molecules which are composed of N-methylpyrrole units (hereinafter also called Py) which is aromatic ring and N-methylimidazole units (hereinafter also called Im) (non-patent documents 15-17). Py and Im, continually coupled and folded, can assume a U-shaped conformation in the presence of γ-aminobutyrate. In the pyrrole-imidazole polyamides related to the present invention, N-methylpyrrole units (Py), N-methylimidazole units (Im) and γ-aminobutyrate units (also called γ-linker) are bound each other by amide bond (—C(=O)—NH—), and the general structure and production methods of the pyrrole-imidazole polyamides are publicly known (patent documents 1-3).

Synthetic polyamides can bind to a specific base pair in the minor groove of double helix DNA with a high affinity and specificity. The specific recognition of a base pair depends on the formation of a one-to-one pair between Py and Im. That is, in the U-shaped conformation in the minor groove of DNA, Py/Im pair targets a C-G base pair, Im/Py targets a G-C base pair, and Py/Py targets both an A-T base pair and a T-A base pair (non-patent documents 16-17). According to a recent study, it becomes clear that as the result of substituting a pyrrole ring of Py/Py pair with 3-hydroxypyrrole (Hp), the A-T condensation can be overcome by binding of Hp/Py preferentially to a T/A pair (non-patent document 18).

In general, the initiation of transcription is considered to be an important point of a gene control. For initiating transcription, several transcription factors are required to bind to specific recognition sequences in the promoter region of a gene. A polyamide in the minor groove may interfere with the gene control by blocking the binding of a transcription factor if the transcription factor plays an important role in the gene expression. This hypothesis has been proven to be correct in in vitro and in vivo experiments. An 8 membered ring Py-Im polyamide, which is bound inside the recognition site of zinc finger (the binding site of TFIIIA), inhibits the transcription of the 5S RNA gene (non-patent document 19). Polyamides that bind to a base pair sequence contiguous to a transcription factor sequence in a promoter of human immunodeficiency virus type 1 (HIV-1) blocks HIV-1 replication in human cells. These sequences include the TATA box, lymphocyte enhancer factor LEF-1 sequence and ETS-1 sequence (non-patent document 20). In contrast to these, a polyamide may also activate expression of a gene, by blocking repressor factor or replacing an original transcription factor (non-patent documents 21-23). UL122 mediated early protein 2 (IE86) of human cytomegalovirus (CMV) blocks the supply of RNA polymerase II to the promoter and inhibits the transcription of the corresponding genes (non-patent document 21). Synthetic polyamides can block the inhibition by IE86 and relieve the expression of the corresponding genes (non-patent document 22). The polyamide designed by Mapp acts as an artificial transcription factor and mediates the transcription reaction of the gene (non-patent document 23).

Patent document 1: Japanese Patent No. 3045706
Patent document 2: JP-A-2001-136974
Patent document 3: WO 03/000683 A1
Non-patent document 1: Piek et al., FASEB J. 13, 2105-2124 (1999)
Non-patent document 2: Bataller R et al. Gastroenterology 118, 1149, 2000
Non-patent document 3: Watanabe, H. et al. Gendai Iryo 35 (No. 2), 2003
Non-patent document 4: Yamamoto T. et al: Kidney Int 49: 461, 1996
Non-patent document 5: Border W A et al: Kidney Int 51: 1388, 1997
Non-patent document 6: Ono et al. Circulation 98: 149, 1998
Non-patent document 7: Giri S N al: Thorax 1993
Non-patent document 8: Makino, N et al: Gendai Iryo Vol. 35, No. 2, 2003
Non-patent document 9: Mori et al. J Cell Physiol; 181: 153, 1999
Non-patent document 10: Reilly J et al. Clin Haematol: 11: 751-767, 1998
Non-patent document 11: Martyre M C et al. Br J Haematol 77: 80-86, 1991
Non-patent document 12: Rameshwar P et al. Am J Haematol 59: 133-142, 1998
Non-patent document 13: Rameshwar et al. J Immunol 165: 2271-2277, 2000
Non-patent document 14: Shigeki et al. FASEB J 16: 1967-1969, 2002
Non-patent document 15: Trauger et al: Nature, 1996; 382: 559-61
Non-patent document 16: White et al. Chem Biol. 1997; 4: 569-78
Non-patent document 17: Dervan: Bioorg Med Chem. 2001; 9: 2215-35
Non-patent document 18: White et al: Nature. 1998; 391: 468-71
Non-patent document 19: Gottesfeld et al: Nature. 1997; 387: 202-5
Non-patent document 20: Dickinson et al. Proc Natl Acad Sci USA. 1998; 95: 12890-5
Non-patent document 21: Lee et al. Proc Natl Acad Sci USA. 1996; 93: 2570-5
Non-patent document 22: Dickinson et al: Biochemistry. 1999; 38: 10801-7

Non-patent document 23: Mapp et al. Proc Natl Acad Sci USA. 2000; 97: 3930-5

DISCLOSURE OF THE INVENTION

Problems to be Solved by the Invention

The aforementioned methods using antisense oligodeoxynucleotides and ribozymes have problems in that the target sequence is limited, the transfer of the antisense oligodeoxynucleotides and ribozymes to tissues and cells is inefficient, and they are prone to degradation by ribonuclease. Up until now, there is no report on TGF-β gene expression inhibitor using pyrrole-imidazole polyamides which bind to the hTGF-β gene base sequence, or a therapeutic drug for diseases related to TGF-β.

Means for Solving the Problems

The present inventors have tried hard to develop pyrrole-imidazole polyamides which inhibit the expression of human TGF-β gene by binding specifically to a particular region of the human TGF-β promoter and to study its pharmacological effect. To obtain a compound that can inhibit the expression of human transforming growth factor-β1 (hTGF-β1) gene and that can also be useful as a therapeutic drug, the present inventors have studied polyamides targeting various fragments of the hTGF-β1 promoter and found that a compound, which binds to the base pair sequence from −557 to −536 of the hTGF-β1 promoter adjacent to the fat-specific element 2 (FSE2) sequence, inhibited the activity of the hTGF-β1 promoter significantly and downregulated the expression of the hTGF-β1 gene in cultured human vascular smooth muscle cells (VSMC) to complete the present invention.

That is, the present invention is described as follows.

(1) A TGF-β gene expression inhibitor comprising a pyrrole-imidazole polyamide containing: an N-methylpyrrole unit (hereinafter also referred to as Py), an N-methylimidazole unit (hereinafter also referred to as Im) and a γ-aminobutyrate unit, wherein said pyrrole-imidazole polyamide can be folded into a U-shaped conformation at the γ-aminobutyrate unit in a minor groove of a double helix region (hereinafter referred to as target region) which comprises a part or all of the following base sequence from −557 to −536 (SEQ ID NO: 1) in a human transforming growth factor β1 (hereinafter also referred to as hTGF-β1) promoter, and a complementary strand thereof:

(SEQ ID NO: 1)
TAAAGGAGAGCAATTCTTACAG wherein a Py/Im pair corresponds to a C-G base pair, an Im/Py pair corresponds to a G-C base pair, and a Py/Py pair corresponds to both an A-T base pair and a T-A base pair.

(2) The TGF-β gene expression inhibitor according to (1), further comprising a β-alanine unit.

(3) The TGF-β gene expression inhibitor according to (1) or (2), wherein said target region is a double helix region comprising a part or all of the following base sequence from −548 to −537 (SEQ ID NO: 2) in the hTGF-β1 promoter, and a complementary strand thereof, (SEQ ID NO: 2)
GCAATTCTTACA.

(4) The TGF-β gene expression inhibitor according to (3), wherein said target region is a double helix region which comprises a part or all of the following base sequence from −544 to −538 (SEQ ID NO: 3) in the hTGF-β1 promoter, and a complementary strand thereof, (SEQ ID NO: 3)
TTCTTAC.

(5) The TGF-β gene expression inhibitor according to (1), wherein said pyrrole-imidazole polyamide is represented by the following formula:

[Formula 1]

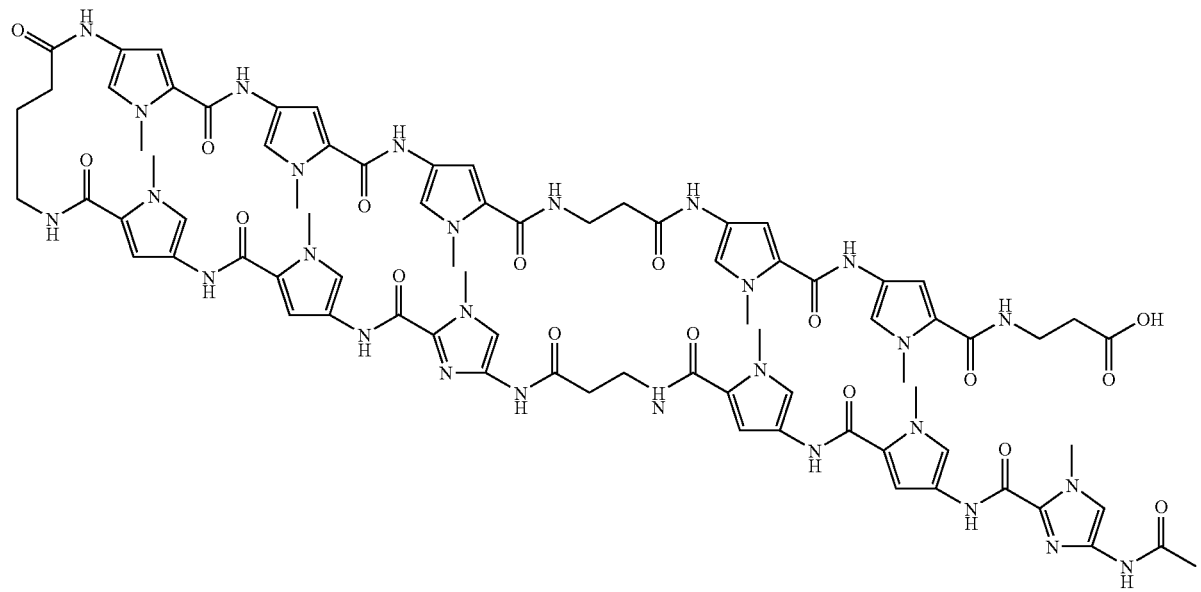

(6) The TGF-β gene expression inhibitor according to (5), wherein the terminal carboxyl group of said pyrrole-imidazole polyamide forms an amide.

(7) The TGF-β gene expression inhibitor according to (6), wherein said amide is an amide formed with N,N-dimethylaminopropylamine.

(8) The TGF-β gene expression inhibitor according to any one of (5) to (7), wherein said pyrrole-imidazole polyamide forms a conjugate with FITC (fluorescein-isothiocyanate).

(9) A pyrrole-imidazole polyamide represented by the following formula:

respectively). The complexes thus obtained were electrophoresed on a 20% polyacrylamide gel and visualized by autoradiography.

FIG. 4 shows that FITC labeled polyamide remains in the nucleus of cultured hVSMC cells after incubating for 2 hr at a concentration of $10^{-9}$ M. FITC labeled polyamide can remain in the nucleus of cultured hVSMC cells more than 48 hr. FITC labeled polyamide was added directly to the culture medium at the concentration of $10^{-9}$ M and observed under a fluorescent microscope.

[Formula 2]

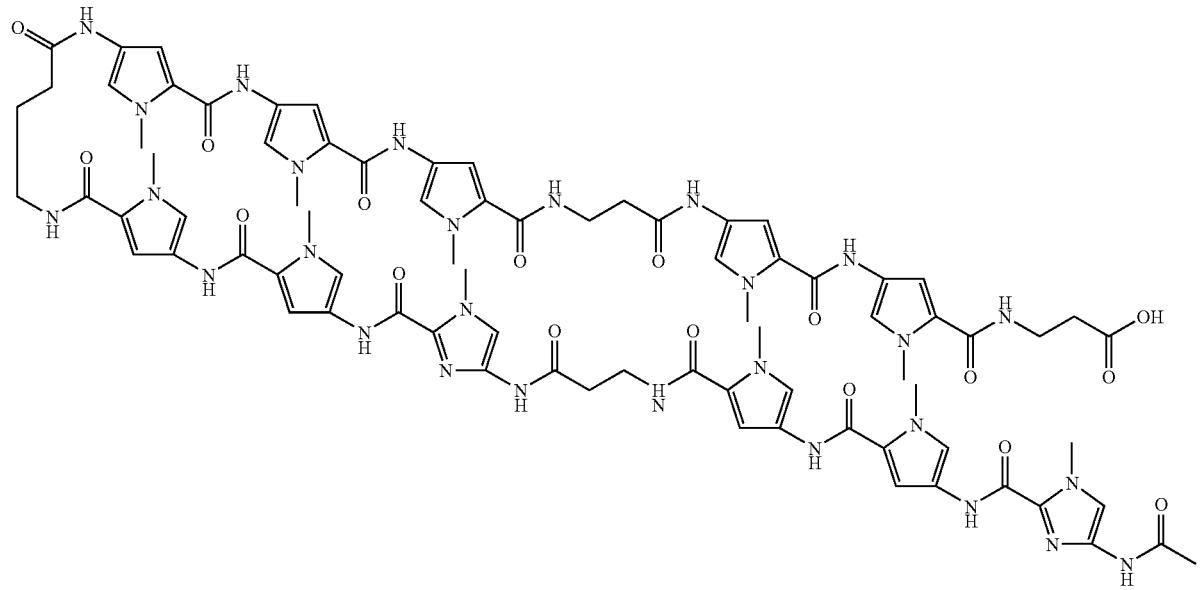

EFFECT OF THE INVENTION

According to the present invention, a TGF-β gene expression inhibitor can be obtained which has no side effects as made by chemotherapeutic agents because a gene expression may specifically inhibited and there is no drawback as degradation by ribonuclease because it is a chemical compound.

BRIEF DESCRIPTION OF THE DRAWINGS

FIG. 6 shows that the polyamide inhibits the expression of the luciferase gene in a plasmid experiment (pGL/TGF). TPA promoted the hTGF-β1 promoter activity, the polyamide (pol) lowered the hTGF-β1 promoter activity, but mismatch polyamide (Mis) did not lower the activity. One microgram of the luciferase gene which was controlled by the hTGF-β1 promoter was transfected for 6 hr in sterilized medium using lipofectin reagent. After 24 hr of the transfection, cells were incubated for 24 hr in a medium containing 0.5% CS in the presence (or absence) of the polyamide or the mismatched polyamide, and the luciferase activity was assayed in these cells extracts using a dual luciferase/reporter gene assay system. One hundred μL of luciferase substrate was mixed with 20 μL cell extracts. After the mixing, the reaction mixture was placed in a luminometer (Turner Designs-Bioblock, Illkirch, France), and the light emitted for ten seconds at room temperature was measured. PMA was used as a positive control. Comparison with the control *P<0.05.

SEQUENCE TABLE FREE TEXT

Figure 1:
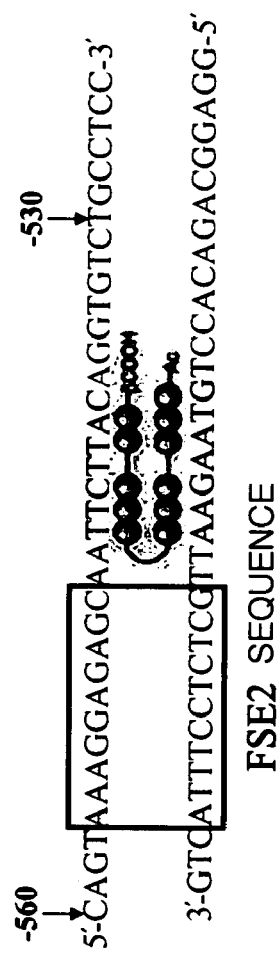
FIG. 1 shows the structure of a synthetic Py-Im polyamide used in the present invention (SEQ ID NOs: 8 and 9).

SEQ ID NO: 4 Sense primer
SEQ ID NO: 5 Antisense primer
SEQ ID NO: 6 Sense primer
SEQ ID NO: 7 Antisense primer

BEST MODE FOR CARRYING OUT THE INVENTION

In the pyrrole-imidazole polyamide related to the present invention, N-methylpyrrole units (hereinafter also called Py), N-methylimidazole units (hereinafter also called Im) and γ-aminobutyrate units (also called γlinker) are bound each other by amide bond (—C(═O)—NH—), and the general structure and the methods for manufacturing of the pyrrole-imidazole polyamide are publicly known (patent documents 1-3).

For example, pyrrole-imidazole polyamides can be easily synthesized by an automated synthesizer using Fmoc (9-fluorenylmethoxycarbonyl) on solid phase (solid phase Fmoc method) (patent document 3). Since pyrrole-imidazole polyamides can be cut out from the solid carrier with carboxylic acid residue at the terminal end by the solid phase Fmoc method, derivatives of pyrrole-imidazole polyamides can be produced by introducing various functional groups to the termini of the molecules. Compounds with DNA alkylating activity, for example, duocarmycin, pyrrolobenzodiazepine, bleomycin, enediyne compounds, nitrogen mustard, derivatives thereof and the like, can be introduced as necessary. Since the solid phase Fmoc method is automated by using commercially available protein (peptide) synthesizers, conjugates with natural or non-natural protein with pyrrol-imidazole polyamides can be synthesized. Further, since the reaction condition is milder in the Fmoc method than in the t-BOC method, it is possible to introduce organic compounds other than protein (including compounds with functional groups that are unstable under an acidic condition). For example, conjugates of pyrrole-imidazole polyamides with DNA or RNA (or the derivatives thereof) may be synthesized automatically.

According to the publicly known Fmoc methods and the like described above, pyrrole-imidazole polyamides having terminal carboxylic group can be synthesized. The specific example includes pyrrole-imidazole polyamides having a β-alanine residue (β-aminopropionate residue) and γ-aminobutyrate residue at the terminus. Pyrrole-imidazole polyamides having a alanine residue and γ-aminobutyrate residue at the terminus can be synthesized, for example, by the solid phase Fmoc method using a peptide synthesizer with solid phase carriers holding aminopyrrolecarboxylic acid, aminoimidazolecarboxylic acid, β-alanine or γ-aminobutyrate in each of which amino groups are protected by Fmoc.

Specific examples of aminopyrrolecarboxylic acid include, for example, 4-amino-2-pyrrolecarboxylic acid, 4-amino-1-methyl-2-pyrrolecarboxylic acid, 4-amino-1-ethyl-2-pyrrolecarboxylic acid, 4-amino-1-propyl-2-pyrrolecarboxylic acid, 4-amino-1-butyl-2-pyrrolecarboxylic acid and the like. Specific examples of aminoimidazolecarboxylic acid include, for example, 4-amino-2-imidazolecarboxylic acid, 4-amino-1-methyl-2-imidazolecarboxylic acid, 4-amino-1-ethyl-2-imidazolecarboxylic acid, 4-amino-1-propyl-2-imidazolecarboxylic acid, 4-amino-1-butyl-2-imidazolecarboxylic acid and the like.

By the solid phase Fmoc method, for example, a conjugate of pyrrole-imidazole polyamide and FITC (fluorescein isothiocyanate) can be synthesized. Since FITC is known to be a fluorescent labeling reagent, the conjugate obtained may be used to prove that the pyrrole-imidazole polyamide recognizes a specific DNA.

The TGF-β gene expression inhibitor of the present invention comprises a pyrrole-imidazole polyamide containing an N-methylpyrrole unit (Py), an N-methylimidazole unit (Im) and a γ-aminobutyrate unit which can be folded into a U-shaped conformation at the afore-mentioned γ-aminobutyrate unit in the minor groove in a double helix region (hereinafter referred to as target region) which comprises a part or all the sequence from the −557 to −536 (SEQ ID NO: 1) in an hTGF-β1 promoter and a complementary strand thereof, wherein a Py/Im pair corresponds to a C-G base pair, an Im/Py pair corresponds to a G-C base pair, and Py/Py pairs correspond to an A-T base pair and a T-A base pair.

Generally DNA helix backbone forms 2 kinds of grooves. A wide and deep groove is called as a major groove and a narrow and shallow groove is called a minor groove. The aforementioned pyrrole-imidazole polyamide can bind to the minor groove which is formed by specific base pairs, with a high affinity and specificity through non-conjugated bond. The Py/Im pair, Im/Py pair, and Py/Py pair of pyrrole-imidazole polyamide corresponding bind to C-G base pair, G-C base pair, and both A-T and T-A base pair of the minor groove, respectively. And the molecule of pyrrole-imidazole polyamide is folded at the site of γ-aminobutyrate unit to form a U-shaped conformation.

When the base pair in the minor groove does not correspond to the Py and Im pair of pyrrole-imidazole polyamide, the binding of the pyrrole-imidazole polyamide to the minor groove will be insufficient. In the present specification, the pyrrole-imidazole polyamide, which is not corresponding to the base pair of the minor groove as described above, is called a mismatch or a mismatched polyamide.

According to the in vitro studies, Py-Im polyamides are effective inhibitors or activators of general or tissue specific transcription factors (non-patent documents 19-23). Drosophila sometimes acquires a functional phenotype or loses it without particular toxicity in the presence of a specific polyamide. This is the result of specific control of the gene expression by the polyamide (Janssen et al. Mol Cell. 2000; 6:

1013-24; Janssen et al. Mol Cell. 2000; 6: 999-1011.). The present inventors synthesized Py-Im. polyamides targeting the specific fragment of the hTGF-β1 promoter. As shown exactly in FIG. 4, the FITC labeled Py-Im polyamides pass through the cell membrane spontaneously, and when the Py-Im polyamide was added to the culture medium of hVSMC culture, it was accumulated in the nuclei at a high concentration. These polyamides stably remained in the nuclei for 48 hr or longer without a particular loss. Compared with the previously described antisense oligonucleotides and ribozymes (Hu W Y, Fukuda N, Nakayama M, Kishioka H, Kanmatsuse K. Inhibition of vascular smooth muscle cell proliferation by DNA-RNA chimeric hammerhead ribozyme targeting to rat platelet-derived growth factor A-chain mRNA. J Hypertens. 2001; 19: 203-12; Teng J, Fukuda N, Hu W Y, Nakayama M, Kishioka H, Kanmatsuse K. DNA-RNA chimeric hammerhead ribozyme to transforming growth factor-beta1 mRNA inhibits the exaggerated growth of vascular smooth muscle cells from spontaneously hypertensive rats. Cardiovasc Res. 2000; 48: 138-47), the polyamides showed a superior permeability (at a low concentration with no need for transfection medium) and a higher stability in cultured hVSMC. The high permeability and stability of polyamides provide an ideal drug delivery to the nuclei of eukaryotic cells for gene therapy.

Up until now the development of Py-Im polyamides has been based on the structural characteristic of the transcription factor-DNA complex in the promoter sequence. The most efficient way of targeting a sequence in the TATA box containing promoter would be to design to target the base pair sequence adjacent to the TATA box. In most protein-encoding genes, the TATA box is located at 25-35 base pair upstream of the transcription initiation site. A transcription associated factor D ($TAF_{II}D$) includes the TATA box binding protein (TBP) which binds to the TATA box specifically and forms a pre-initiation complex (PIC) taking other transcription related factors in core promoter. The PIC initiates transcription of the gene and controls the expression of the genes by interacting with the activator or suppressor. Since TBP binds also to the minor groove of double helix DNA (Lee et al. Cell. 1991 Dec. 20; 67(6): 1241-50; Starr et al: Cell. 1991; 67: 1231-40; Courey et al. Cell. 1988; 55: 887-98.), the synthetic polyamide competitively occupies the binding site of TATA binding protein and interferes the transcription of the gene. It is known that among the polyamides designed on the basis of various promoters, any one targeting the TATA box is always successful (non-patent documents 20, 21).

There are kinds of promoters having neither the TATA box nor initiator region (Inr) (Javahery et al: Mol Cell Biol. 1994; 14: 116-27; Lo et al. Gene. 1996 Dec. 5; 182 (1-2): 13-22; Romeo et al. Gene. 1997; 189: 289-95.). There appears to be a tendency that the gene promoters that are highly expressed with high specificity are likely to have the TATA box but the promoters of the housekeeping genes are lacking it. The promoters without the TATA box may be required for the genes that are expressed at low level or those need to be strictly downregulated during growth phase, but the mechanisms for these promoters are yet to be studied. The promoter of hTGF-β1 belongs to this kind of promoter and contains many positive and negative sequences in the various upstream regions of the transcription initiation site (Kim et al. J Biol Chem. 1989; 264: 402-8.). Several SP-1 and two AP-1 sequences exist adjacent to the transcription initiation site. Since various viral and cellular promoters are activated by SP-1 protein, it would appear that only one SP-1 sequence is sufficient for a promoter to be stimulated by SP-1 (Kadonaga et al: Cell. 1987; 51: 1079-90; Courey et al. Cell. 1988; 55: 887-98.). AP-1 sequence responds with AP-1 transcription factor which is composed of either Jun homodimer or Fos/Jun heterodimer complex. Several substances such as, TPA, v-src gene product and hTGF-β1 itself, stimulate the expression of hTGF-β1 through AP-1 sequence (Kim et al. J Biol Chem. 1989; 264: 7041-5; Kim et al. J Biol Chem. 1989; 264: 19373-8. Kim et al: Mol Cell Biol. 1990; 10: 1492-7; Birchenall-Roberts et al: Mol Cell Biol. 1990; 10: 4978-83.).

Figure 7:
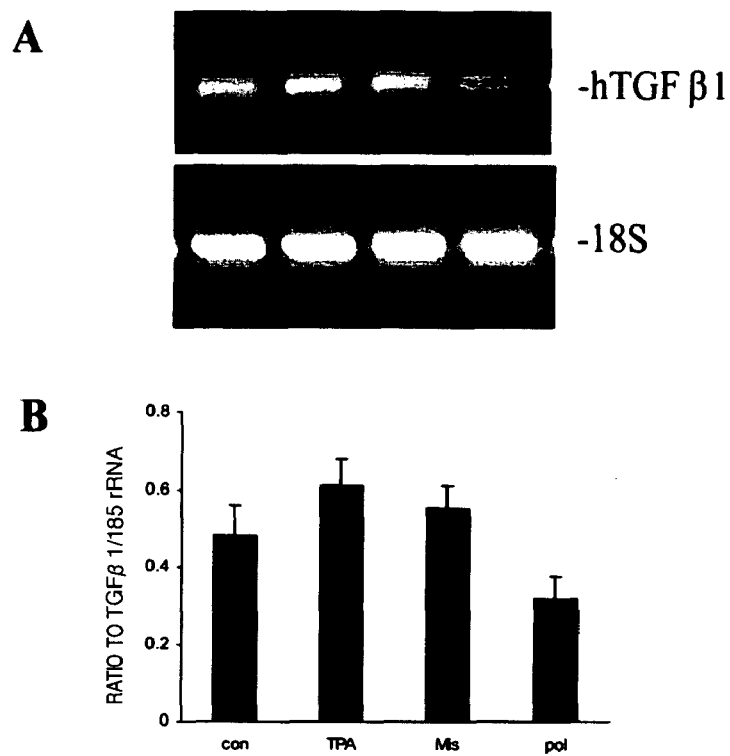
FIG. 7 shows that the polyamide inhibits the expression of hTGFβ1 mRNA in hVSMC cells. $10^{-9}$ M of the polyamide was added to medium of cultured hVSMC and incubated for 24 hr. Treatment with 50 ng/mL of TPA was used as a positive control. Total RNA was extracted from the cells, and single stranded cDNA was produced by reverse-transcription and was amplified with the primers for hTGFβ1 and 18S rRNA as will be described in the section of Materials and Methods. (A) Five microliters of PCR product was separated on a 1.5% agarose gel electrophoresis. (B) TPA stimulated the expression of hTGFβ1 mRNA. The ratio of hTGFβ1 mRNA to 18S rRNA was decreased significantly in the polyamide treated group (pol), but the mismatch polyamid (mis) did not have any effects on the expression of hTGFβ1.
Figure 8:
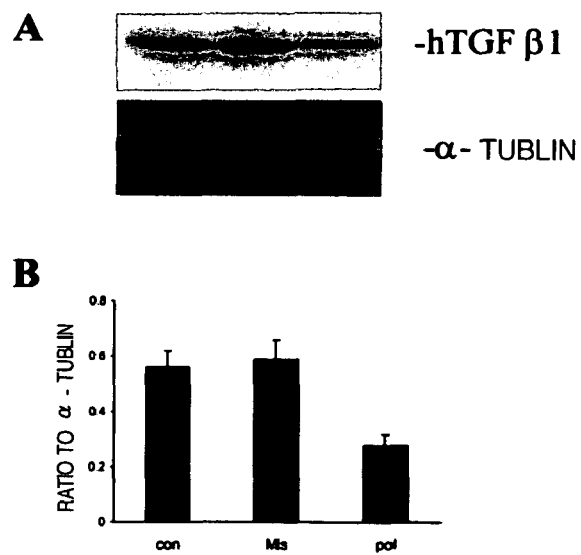
FIG. 8 shows the effect of the polyamide on hTGFβ1 protein in cultured hVSMC. $10^{-9}$ M of the polyamide was added to medium of cultured hVSMC and incubated for 24 hr. (A) The expression of hTGFβ1 protein was investigated by Western blot analysis. (B) The polyamide (pol) inhibited significantly hTGFβ1 protein in cultured hVSMC but the mismatch (mis) did not.

It is hypothesized that the sequence of SP-1 and/or AP-1 mediates the activation of the expression of the hTGF-β1 gene. The important polyamides are designed so as to target base pairs adjacent to the different sequences of AP-1 and SP-1 to block the bonding of a responsive transcription factor. However, there is no data enough to show whether these polyamides can inhibit or activate the hTGF-β1 promoter. These results may be due to that the site occupied by the designed polyamides in the minor groove of DNA and the like is not suitable. The present inventors have expanded the target sequence to the upstream of the hTGF-β1 promoter. One of the polyamides targets the base pair sequence from −544 to −538 of the hTGF-β1 promoter, and it is shown that this inhibits the promoter activity in vitro (FIGS. 5-7) and hTGF-β1 mRNA and a protein in hVSMC culture (FIGS. 7, 8). The base pair sequence from −544 to −538 of the hTGF-β1 promoter is located next to the fat-specific element 2 (FSE2) sequence (FIG. 1). FSE2 shows an inhibitory activity on the expression of the adipocyte P2 (aP2) gene in preadipocytes, and preadipocytes contain more FES2 sequence binding protein than adipocytes (Kadonaga et al. Cell. 1987; 51: 1079-90; Courey et al. Cell. 1988; 55: 887-98.). Transcription repressor that suppresses a transcription has been discovered from the core promoter containing a TATA box, but not found in the promoter without TATA (Aso et al: EMBO J. 1994; 13: 435-45; Mack et al. Nature. 1993; 363: 281-3; Merino et al. Nature. 1993; 365: 227-32.). It has been believed that these transcriptional repressors interfere the interaction of TBP-TATA and then inhibit the transcription of the gene. Combination of these data concerning the repressor suggests a hypothesis that the suppressive function of FSE-2 sequence in adipocytes is mediated by the TATA box. Since hTGF-β1 promoter does not contain the TATA box, it is considered that the function of FSE2 sequence in hTGF-β1 is different from that of the aP2 gene. Since expression of almost all the genes of mammalians highly tends to depend on the combination of actions of a large number of proteins that are bound to the promoter and enhancer sequences, the simplest model to explain the present results is that the pyrrole-imidazole polyamide of the present invention blocks the interaction of the transcription factor and DNA in the FSE2 sequence region and shows an inhibitory effect on the hTGF-β1 promoter activity.

Other than the regulation by the transcription factor in the promoter region, there is a possibility that other factors may also affect the expression of the gene. These factors include chromatin packing, polyadenylation, splicing, mRNA stability, initiation of translation and the like (Berger et al. Mol Cell. 2001; 5: 263-8; McKeown Annu Rev Cell Biol. 1992; 8: 133-55; Decker et al. Trends Biochem Sci. 1994; 19: 336-40; Kozak Annu Rev Cell Biol. 1992; 8: 197-225.). There seems to be a possibility that the synthetic polyamide can approach the target site due to the positioning of nucleosome and has effect on chromatin condensation/decondensation structure by targeting the specific sequence (Gottesfeld et al. J Mol Biol. 2002; 321: 249-63; Gottesfeld et al. J Mol Biol. 2001; 309: 615-29.). It has been proven that a pyrrole-imidazole polyamide opens heterochromatin brown satellite making binding of GAF possible and as a result, causing the change in phenotype in Drosophila melanogaster. Since pyrrole-imidazole polyamides can be easily synthesized and designed to target a sequence of interest, they are useful for studying the genome functions, and ultimately, for gene therapy such as inhibition and activation of the hTGF-β1 gene.

The Py-Im polyamide of the present invention can be designed at an upstream distal to the transcription initiation region, and shows an inhibitory effect on the expression of the hTGF-β1 gene.

EXAMPLE

I. Materials and Methods (1) Design of Py-Im Polyamide Corresponding to the hTGF-β1 Promoter FIG. 1 shows a scheme for producing the compound and its mismatch compound (hereinafter also simply referred to as mismatch) that were used in the present experiment. Py-Im polyamide was designed to bind to the base pair from −544 to −538 of the hTGF-β1 promoter adjacent to the fat-specific element 2 (FSE2).

(2) Machine Assisted, Automated Synthesis of Py-Im Polyamides using Fmoc Method

Machine assisted, automated synthesis of pyrrole-imidazole polyamides were carried out using a continuous flow peptide synthesizer Pioneer (Trademark) (Applied Biosystems, Inc.) at 0.1 mmol scale (200 mg of Fmoc-β-alanine-CLEAR acid resin, 0.50 meq/g, Peptide Institute, Inc.). The automated solid phase synthesis includes the steps of washing with DMF, removal of Fmoc group with 20% piperidine/DMF, washing with methanol, coupling with monomers for 60 min in the presence of HATU and DIEA (4 equivalent each), washing with methanol, protection with anhydrous acetic acid/pyridine, if necessary, and final washing with DMF. Py-Im polyamides were generally obtained in a moderate yield (10-30%).

FITC coupling: Four (4) times excess fluorescein (0.40 mmol) and DIEA (without HATU) dissolved in DMF was passed through a column and flashed for 60 min.

General procedures: After removing the Fmoc group of an Fmoc-β-alanine-Wang resin, the resin was washed continuously with methanol. The coupling step was carried out with an Fmoc amino acid, and then the washing with methanol was carried out. These steps were repeated many times until all the sequence was introduced. After the coupling steps were completed, the amino acid at the N terminal was protected or coupled with FITC if necessary, washing with DMF was carried out and the reaction vessel was detached.

Degradation as carboxylic acid: The synthetic polyamides were isolated by precipitation with cold ethyl ether after the degradation step (91% TFA-3%/TIS-3% DMS-3% water mixture, 5 ml/resin 0.1 mmol).

Degradation as amine: The synthetic polyamides were isolated by precipitation with cold ethyl ether after the degradation step (N,N-dimethylaminopropyl amine 5 ml/resin 0.1 mmol, 50° C., overnight).

Purification: Final purification was carried out with an analytical RP-HPLC at a flow rate of 10 ml/min with a linear gradient of B (acetonitrile) in buffer A (0.1% AcOH/water) using UV detection at 350 nm.

In compounds 4a and 4b below, I, P, β, γ, Dp and Ac represents N-methyl imidazole residue, N-methylpyrrole residue, β-alanine residue, γ-aminobutyrate residue, N,N-dimethylaminopropyl amine and acyl group, respectively.

a) FITC-β-IPP-β-IPP-γ-PPP-β-PP-β Dp (compound 4a)
Gradient: buffer B 15%-45% (30 min), flow rate 10 ml/min. Yield 7 mg (3%).

b) Ac-IPP-β-IPP-γ-PPP-β-PP-βCOOH (compound 4b)
Gradient: buffer B 25%-35% (30 min, 60° C.), flow rate 10 ml/min. Yield 29 mg (17%).

Figure 2A:
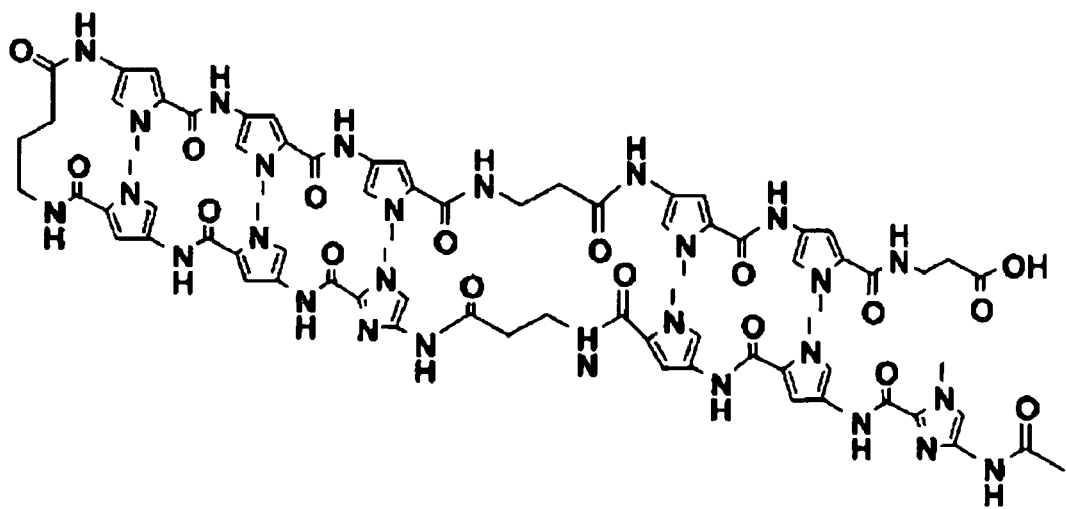
FIG. 2A shows the structure of a synthetic Py-Im polyamide (compound 4b).
Figure 2B:
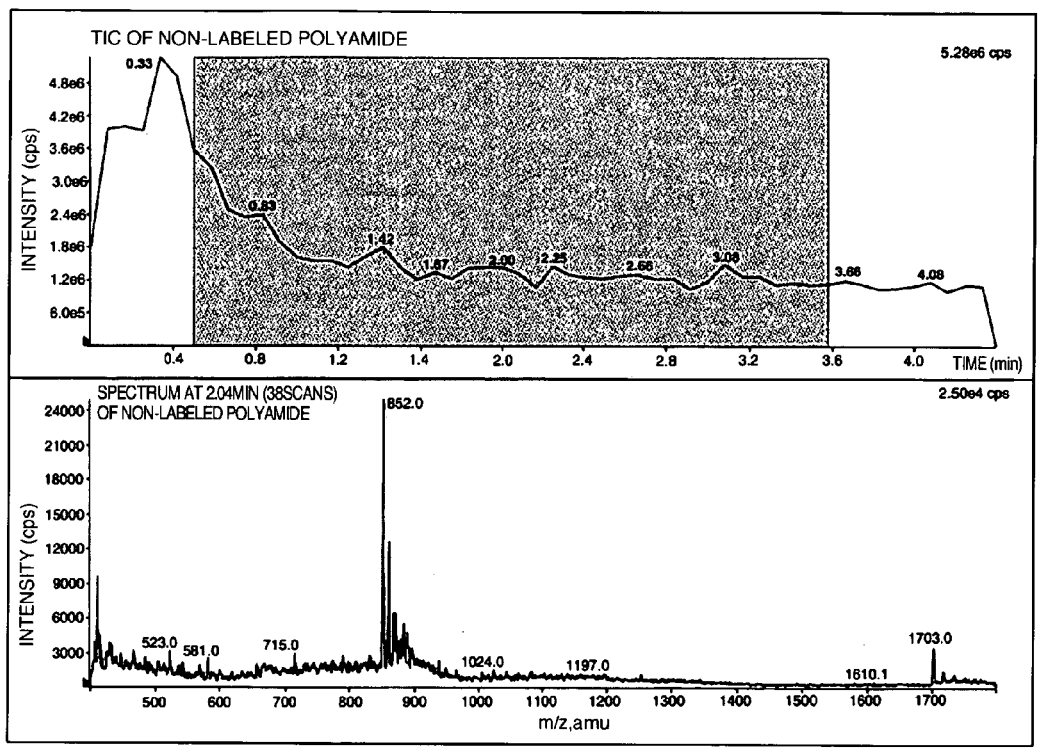
FIG. 2B shows the TIC chart and an electrospray ionized mass spectra of a synthetic Py-Im polyamide (compound 4b).

The structure of Py-Im polyamide (compound 4b) is shown in FIG. 2A and its TIC (total ion chromatogram) chart and electrospray ionized mass spectrum are shown in FIG. 2B. As a mismatch, a polyamide with the structure of Ac-PPP-β-IPP-γ-PPP-β-COOH was used, which was the aforementioned compound 4b in which I adjacent to the acyl group was substituted with P.

(3) hVSMC Cell Culture hVSMC was obtained from Clonetics (Walkersville, Md.). hVSMC was cultured in Dulbecco's modified Eagle's medium (DMEM) containing 10% calf serum (Gibco Life Technologies, Gaithersburg, Md.), 100 U/ml penicillin and 100 mg/ml streptomycin. Cells were passaged by trypsin treatment with 0.05% trypsin (Gibco) in $Ca^{2+}$-free and $Mg^{2+}$-free phosphate buffered saline (PBS) and cultured in 75-$cm^2$ tissue culture flasks. The medium was exchanged every four or five days, and experiments were carried out on cells during 5-10 passages.

(4) Incubation of FITC-Labeled Polyamides in Cultured hVSMC

Passaged hVSMC was cultured at a density of $10^5/cm^2$ for 24 hr in a 24-well flask. FITC-labeled polyamides were directly added to the medium at a concentration of $10^{-9}$ M and observed every one hour under a florescent microscope.

(5) Gel-Shift Assay

Oligonucleotides were synthesized, annealed, and 12 kinds of double stranded oligonucleotides were produced corresponding to the base pairs from −548 to −537 of hTGF-β1 promoter (FIG. 1A). The double stranded DNAs were labeled with [$\gamma$-$^{32}$P]-ATP using T4 polynucleotide kinase, and incubated in a binding buffer (40 mM Tris, pH 7.9, 250 mM NaCl, 25 mM EDTA, 25 mM DTT, 100 mM KCl) with the polyamides or mismatched polyamides at 37° C. for 15 min. The complexes thus obtained were electrophoresed by 20% polyacrylamide gel and visualized by autoradiography.

(6) Construction of Luciferase Gene Expression System under Control by hTGF-β1 Promoter The 2.2 kb fragment containing the hTGF-β1 promoter derived from plasmid phTBG 101 (non-patent document 10) was isolated and inserted to pGL3 basic plasmid (Promega, Madison, Wis.) at the upstream of the coding region of luciferase reporter gene. The accurate structure of the constructed plasmid was identified by spectral analysis with restriction enzymes analysis and sequencing.

(7) In Vitro Transcription Reaction

In vitro transcription reactions were carried out using nuclear extracts of Hela cells and the in vitro transcription system (Promega, Madison, Wis.). Twenty-five microliters of the reaction mixture was composed of 100 ng of DNA template, 8 U of HeLa nuclear extracts, each 400 μM of 3 kinds of non-labeled nucleotide triphosphate (UTP, CTP, GTP), 25 μM of $\gamma$-$^{32}$P-ATP (5 ci/mmol, NEM Life-Science Products), transcription buffer (pH 7.9) containing 20 mM hydroxyethyl piperadinyl ethansulfonic acid (HEPES), 100 mM KCl, 4.0 mM $MgCl_2$, 20% glycerol, 0.2 mM EDTA and 0.6 mM phenyl methyl sulfonyl fluoride. The template DNA for transcription was cleaved with SphI (New England BioLabs, Beverly, Mass.). After incubating the transcription reaction mixture at 30° C. for 60 min, the reaction was terminated by adding 175 μM Hela extracts stop solution (0.3 M Tris-HCl, pH 7.0, 0.3 M sodium acetate, 0.5% SDS, 2.0 mM EDTA, 3 μg/ml tRNA), and then extraction with phenol-chloroform-isoamylalcohol and precipitation with ethanol were carried out. Samples were re-suspended in 98% formaldehyde loading dye and electrophoresed in a 7 M urea 6% polyacrylamide gel after heating at 90° C. for 10 min. The gel was dried and bands were visualized by autoradiography.

(8) Transient Transfection and the Luciferase Assay hVSMC cells were cultured at a density of $10^{-5}/cm^2$ in 24 well plates in the presence of 10% CS. After 24 hr, the reporter gene that was driven by the hTGF-β1 promoter was transfected using Lipofectin reagent (GibcoBRL) in the presence of 1 μg DNA in the sterilized medium, according to the method indicated by the manufacturer. Cells were incubated with the DNA liposome complex for 6 hours, and then the medium was exchanged to 1 ml of fresh complete medium. After 24 hr of the transfection, cells were incubated for 24 hr in the presence or absence of a polyamide or a mismatch polyamide, in the medium containing 0.5% CS. At the end of the treatment, the medium was removed and cells were scraped off and suspended in 150 μl of Passive Lysis buffer. After brief centrifugation, luciferase activity in the cell extracts was measured using a dual-luciferase reporter gene assay system (Promega, Madison, Wis.). One hundred microliters of luciferase substrate was added to 20 μl of the extract. After mixing, the reaction mixture was placed in a luminometer (Turner Designs-Bioblock, Illkirch, France), and the light emitted for ten seconds at room temperature was measured.

(9) RNA Extraction, and Reverse Transcription Reaction and Polymerase Strand Reaction (RT-PCR) Assay for Growth Factor mRNA Cultured cells were washed with PBS, dissolved in 800 μL of RNAzolB (Biotex Laboratories, Inc., Houston, Tex.), mixed with 80 μL of chloroform and centrifuged. The colorless upper aqueous phase was mixed with an equal volume of isopropanol to precipitate RNA. RNA pellet was washed twice with 500 μL of 75% ethanol and, after drying, dissolved in 10 μL of TE buffer. After denaturing at 65° C. for 15 min, the RNA sample was treated with 0.5 U DNase (Gibco) in 0.5 ml of DNase buffer (20 mM Tris-HCl pH 8.3, 50 mM KCl, 2.5 mM $MgCl_2$) at room temperature for 45 min. DNase was denatured by adding 0.5 ml of 0.5M EDTA and heating at 98° C. for 10 min.

RNA aliquots of an equal amount (1 μg/20 μL) were reverse transcribed to single stranded cDNAs using 2.5 U/20 μL of avian myeloblastosis virus reverse transcriptase (Takara Biochemicals, Osaka, Japan) in 10 mM Tris-HCl (pH 8.3), 5 mM $MgCl_2$, 50 mM KCl, 1 mM deoxy NTPs and 2.5 μM random hexamers. Two microliters of the diluted cDNA product was made up to 25 μl by mixing with 10 mM Tris-HCl (pH 8.3), 50 mM KCl, 4 mM $MgCl_2$, 0.025 U/μL Taq DNA polymerase (Takara Biochemicals, Osaka, Japan), and 0.2 μM each of the upstream sense primer and downstream antisense primer. The sense primer (5'-ATCAGAGCTCCGAGAAGCGGTACC-3')(SEQ ID NO: 4) and the antisense primer (5'-GTCCACTTGCAGTGTTATCCTG-3') (SEQ ID NO: 5) were used for PCR amplification of hTGF-β1 mRNA. For human 18S ribosomal RNA, the sense primer (5'-TCAAGAACGAAAGTCGGACG-3')(SEQ ID NO: 6) and the antisense primer (5'-GGACATCTAAGGGCATCACA-3') (SEQ ID NO: 7) were used as the internal control. PCR was carried out with an automatic heat controller (Perkin Elmer, Foster, Calif.). The PCR conditions were: initial denaturation, at 94° C. for 2 min; 30 cycles of denaturation at 94° C. for 1 min, annealing at 58° C. for 1 min and extension at 72° C. for 1 min; last extension at 72° C. for 1 min. As an internal control, PCR with primers for 18S rRNA was included in each reaction. To confirm that the genomic DNA was not amplified by PCR, the control RT-PCR experiment was carried out without reverse transcriptase and with primer sets. In any of the reaction no product was amplified. For semi-quantitative analysis of mRNA, the kinetics of PCR was monitored. The cycle numbers where the PCR products became detectable on the gel were compared among various samples. cDNA samples 10-fold serially diluted (100, 10 and 1 ng) were amplified. PCR products became detectable at earlier cycles by increasing the amount of cDNA. The amount of PCR product corresponding to each target mRNA was increased linearly at 20-35 cycles. Five micromoles (μM) of the PCR product was separated on a 1.5% agarose gel by electrophoresis. The intensity of the bands was measured by computer analysis using NIH software.

(10) Cell Preparation and Western Blot Analysis

Test VSMC and control VSMC were incubated in 6-well plates for 24 hr, washed twice with PBS and incubated on ice in 300 μL of lysis buffer (50 mM Tris-HCl (pH 8.0), 150 mM NaCl, 1 mM EDTA, 1 mM phenylmethylsulfonyl fluoride, 1 μg/mL aprotinin, 1% Triton X-100) for 30 min. Cells were scraped into a 1.5 mL tube and centrifuged, and the supernatant was collected. The protein content of the supernatant was assayed by Bradford protein assay using BIO-RAD protein assay kit (Bio-Rad Lab, Hercules, Calif.). The supernatant contained 20 μg of total protein, which was denatured at 100° C. for 3 min in the loading buffer, electrophoresed on a 10% polyacrylamide gel and transferred to a nitrocellulose membrane. The membrane was incubated at room temperature for 1 hr with mouse monoclonal antibody with specificity to hTGF-β1 (1:500) (R&D systems, Minneapolis, Minn.), and then incubated at room temperature for 1 hr with anti-mouse HRP conjugated secondary antibody at 1:2000. After washing sufficiently, the membrane was incubated with an electrochemical luminescence substrate (Amersham Life Service, Buckinghamshire, UK) and exposed to an X-ray film.

(11) Statistical Analysis

The results were expressed in mean value±SEM. The significance of the difference among the mean values was evaluated by Student's t test. $P<0.05$ was regarded as significant.

Figure 3:
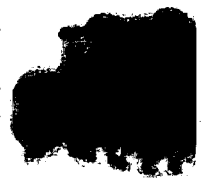
FIG. 3 shows the formation of a polyamide-oligonucleotide complex through binding of a synthetic Py-Im polyamide to the corresponding double stranded oligonucleotide. The double stranded DNA corresponding to the base pair sequence from −548 to −537 of the hTGF-β1 promoter (FIG. 1) was labeled by T4 polynucleotide using [γ-$^{32}$P]-ATP and incubated in a binding buffer at 37° C. for 15 min together with mismatch polyamide (lane 0) or with increasing amount of the polyamide (lane 1, 2 and 3 was 1 nM, 2 nM and 4 nM, FIG. 5 shows that the polyamide inhibits transcription of the luciferase gene in vitro transcription reaction. One microgram of a plasmid was incubated in the transcription buffer with 8 U of HeLa nucleus extract, 3 kinds of non-labeled nucleotide triphosphates (UTP, CTP, GTP) at 400 mM each, and 25 μM α-$^{32}$P-ATP at 30° C. for 60 min. The reaction was terminated by adding 175 μl of HeLa extract stop solution, and then phenol-chloroform-isoamyl alcohol extraction and ethanol precipitation were carried out. Samples were re-suspended in 98% formaldehyde loading dye and heated at 90° C. for 10 min before loading a 6%, 7 M urea-polyacrylamide gel. The gel was dried and visualized by autoradiography.

II. Result (1) Binding of the Synthetic Polyamide to Double Stranded Oligonucleotide At first it was checked whether the synthetic Py-Im polyamides (compounds 4a and 4b) could bind to the corresponding base pairs. Either of the polyamides was able to bind to the corresponding 12 base pairs double stranded oligonucleotide (FIG. 3, lanes 2-4), but the mismatch polyamide failed to bind to these oligonucleotides (FIG. 3 lane 1).

(2) Permeability Through the Cell Membrane and Incorporation into the Nuclei of the Synthetic Polyamides To demonstrate that the synthetic compounds were incorporated into the nuclei and remained in a stable condition in living cells, Py-Im polyamides were labeled with FITC. When the FITC labeled polyamides was incubated for 2 hr in a culture medium at a concentration of $10^{-9}$ M, this FITC was detected in the nuclei of cultured hVSMC at a high density (FIG. 4). This high accumulation of the FITC labeled polyamide in the nuclei was due to non-specific binding in the genome and the concentration of this compound in the cytoplasm was very much lower.

(3) Inhibition of the hTGF-β1 Promoter Activity by the Synthetic Polyamides In vitro transcription system transcribes the DNA code in the presence of HeLa nuclei extract and hTGF-β1 promoter. Since the synthetic polyamides (pol) bind to the base pairs from −544 to −538 of the hTGF-β1 promoter, they reduce transcription. On the other hand, the mismatch polyamide (Mis) did not show any significant effect on the formation of the transcription molecules (FIG. 5).

In the plasmid transfection experiments, the reporter gene that codes for luciferase was driven by the hTGF-β1 promoter and expressed in cultured hVSMC. 12-O-tetradecanoyl-phorbol-13-acetyltransferase (TPA) stimulated the expression of luciferase protein. Incubating with $10^{-9}$ M of the polyamide significantly downregulated the expression of luciferase but the mismatch polyamide had no effect on the expression of the luciferase gene (FIG. 6).

(4) Inhibition of hTGF-β1 mRNA in hVSMC by the Synthetic Polyamide

To observe the effect of the polyamide on the expression of the hTGF-β1 gene in vivo, cultured hVSMC was incubated with $10^{-9}$ M polyamide for 24 hr. hTGF-β1 mRNA was analyzed with RT-PCR method. TPA was used as a positive control. TPA at 50 ng/mL significantly stimulated the expression of hTGF-β1 mRNA. The polyamide of the present invention (pol) inhibited the expression of hTGF-β1 mRNA induced by TPA, but the mismatched polyamide (Mis) did not (FIG. 7).

(5) Effect of the Synthetic Polyamide on the Expression of hTGF-β1 Protein in hVSMC The present inventors checked the effect of the synthetic polyamide (pol) on the expression of hTGF-β1 protein in hVSMC. The synthetic polyamide at $10^{-9}$ M inhibited the expression of hTGF-β1 protein after 24 hr incubation, but the mismatched polyamide (Mis) did not (FIG. 8).

INDUSTRIAL APPLICABILITY

The TGF-β gene expression inhibitor of the present invention can be used as a therapeutic drug for diseases related to TGF-β production.

FREE TEXT IN SEQUENCE LISTING

SEQ ID NO: 4 Sense primer
SEQ ID NO: 5 Antisense primer
SEQ ID NO: 6 Sense primer
SEQ ID NO: 7 Antisense primer

The invention claimed is:

1. A TGF-β gene expression inhibitor comprising a pyrrole-imidazole polyamide containing: an N-methylpyrrole unit (hereinafter also referred to as Py), an N-methylimidazole unit (hereinafter also referred to as Im) and a γ-aminobutyrate unit, wherein said pyrrole-imidazole polyamide can be folded into a U-shaped conformation at the γ-aminobutyrate unit in a minor groove of a double helix region (hereinafter referred to as target region) which comprises all of the following base sequence from −557 to −536 (SEQ ID NO: 1) in a human transforming growth factor β1(hereinafter also referred to as hTGF-β1) promoter, and a complementary strand thereof:

(SEQ ID NO: 1)
TAAAGGAGAGCAATTCTTACAG wherein a Py/Im pair corresponds to a C-G base pair, an Im/Py pair corresponds to a G-C base pair, and a Py/Py pair corresponds to both an A-T base pair and a T-A base pair, wherein said pyrrole-imidazole polyamide is represented by the following formula:

[Formula 1]

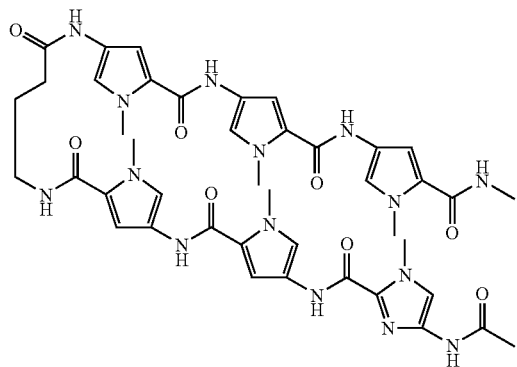

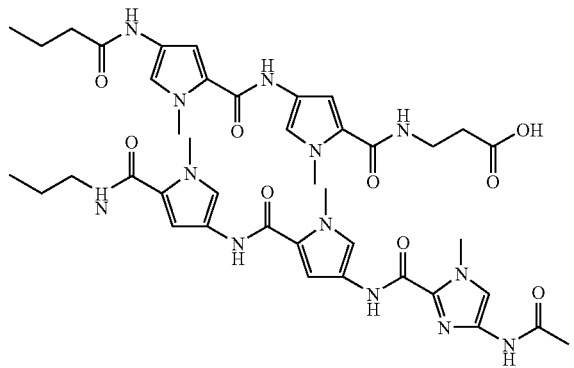

wherein the terminal carboxyl group of said pyrrole-imidazole polyamide optionally is an amide, wherein the optional amide is an amide of the compound represented by Formula 1 with N,N-dimethylaminopropylamine, and said pyrrole-imidazole polyamide is optionally bonded to fluorescein-isothiocyanate.

2. The TGF-β gene expression inhibitor according to claim 1, wherein the terminal carboxyl group of said pyrrole-imidazole polyamide is the amide.

3. The TGF-β gene expression inhibitor according to claim 2, wherein said amide is bonded to N,N-dimethylaminopropylamine.

4. The TGF-β gene expression inhibitor according to any one of claims 1 to 3, wherein said pyrrole-imidazole polyamide forms a conjugate with fluorescein-isothiocyanate.

5. A pyrrole-imidazole polyamide represented by the following formula:

[Formula 2]

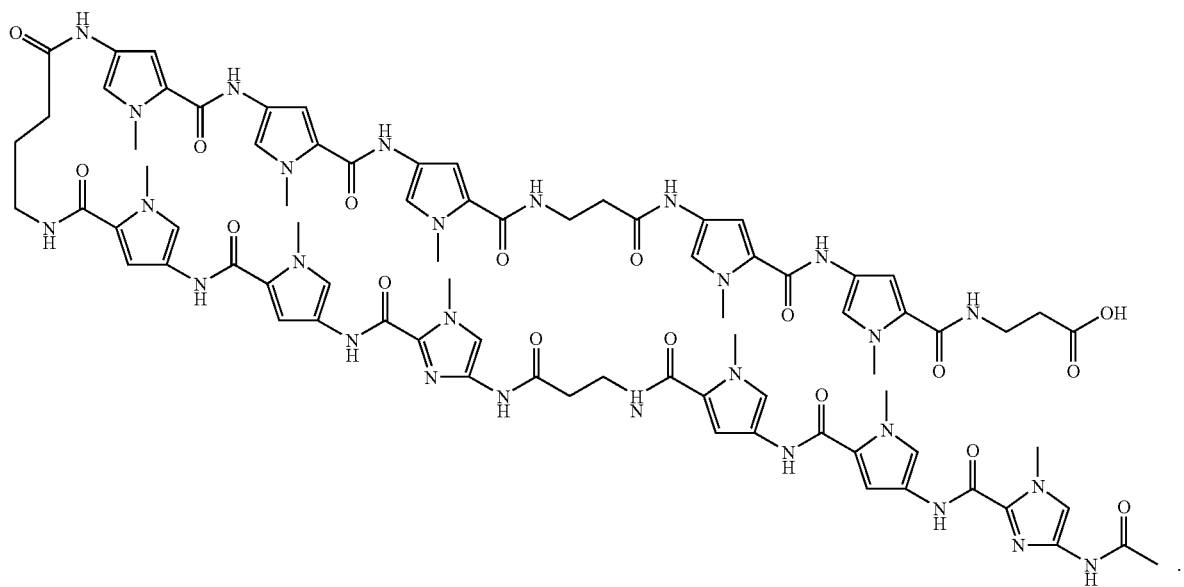

* * * * *

```
SEQUENCE LISTING

<160> NUMBER OF SEQ ID NOS: 9

<210> SEQ ID NO 1
<211> LENGTH: 22
<212> TYPE: DNA
<213> ORGANISM: Homo sapiens

<400> SEQUENCE: 1
taaaggagag caattcttac ag                                            22

<210> SEQ ID NO 2
<211> LENGTH: 12
<212> TYPE: DNA
<213> ORGANISM: Homo sapiens

<400> SEQUENCE: 2
gcaattctta ca                                                       12

<210> SEQ ID NO 3
<211> LENGTH: 7
<212> TYPE: DNA
<213> ORGANISM: Homo sapiens

<400> SEQUENCE: 3 ttcttac                                                              7

<210> SEQ ID NO 4
<211> LENGTH: 24
<212> TYPE: DNA
<213> ORGANISM: Artificial Sequence
<220> FEATURE:
<223> OTHER INFORMATION: Description of Artificial Sequence: Synthetic
      sense primer

<400> SEQUENCE: 4
```

-continued

```
atcagagctc cgagaagcgg tacc                                          24

<210> SEQ ID NO 5
<211> LENGTH: 22
<212> TYPE: DNA
<213> ORGANISM: Artificial Sequence
<220> FEATURE:
<223> OTHER INFORMATION: Description of Artificial Sequence: Synthetic
      sense primer

<400> SEQUENCE: 5
gtccacttgc agtgttatcc tg                                            22

<210> SEQ ID NO 6
<211> LENGTH: 20
<212> TYPE: DNA
<213> ORGANISM: Artificial Sequence
<220> FEATURE:
<223> OTHER INFORMATION: Description of Artificial Sequence: Synthetic
      sense primer

<400> SEQUENCE: 6
tcaagaacga aagtcggacg                                               20

<210> SEQ ID NO 7
<211> LENGTH: 20
<212> TYPE: DNA
<213> ORGANISM: Artificial Sequence
<220> FEATURE:
<223> OTHER INFORMATION: Description of Artificial Sequence: Synthetic
      sense primer

<400> SEQUENCE: 7
ggacatctaa gggcatcaca                                               20

<210> SEQ ID NO 8
<211> LENGTH: 37
<212> TYPE: DNA
<213> ORGANISM: Homo sapiens

<400> SEQUENCE: 8
cagtaaagga gagcaattct tacaggtgtc tgcctcc                            37

<210> SEQ ID NO 9
<211> LENGTH: 37
<212> TYPE: DNA
<213> ORGANISM: Homo sapiens

<400> SEQUENCE: 9
ggaggcagac acctgtaaga attgctctcc tttactg                            37
```